US00PP17022P2

(12) United States Plant Patent
Arts

(10) Patent No.: US PP17,022 P2
(45) Date of Patent: Aug. 22, 2006

(54) POINSETTIA PLANT NAMED 'STARGAZER'

(50) Latin Name: *Euphorbia pulcherrima*
Varietal Denomination: Stargazer

(75) Inventor: Niels Arts, Aalsmeer (NL)

(73) Assignee: Agriom B.V., DeKwakel (NL)

( * ) Notice: Subject to any disclaimer, the term of this patent is extended or adjusted under 35 U.S.C. 154(b) by 24 days.

(21) Appl. No.: 11/146,217

(22) Filed: Jun. 6, 2005

(51) Int. Cl.
*A01H 5/00* (2006.01)

(52) U.S. Cl. ..... Plt./307

(58) Field of Classification Search ..... Plt./307
See application file for complete search history.

(56) References Cited

PUBLICATIONS

GTITM UPOVROM Citation for 'Stargazer' as per QZ PBR 20040582; Apr. 16, 2004.*

* cited by examiner

*Primary Examiner*—Kent Bell
(74) *Attorney, Agent, or Firm*—C. A. Whealy

(57) ABSTRACT

A new and distinct cultivar of Poinsettia plant named 'Stargazer', characterized by its upright and uniform plant habit; vigorous growth habit; dark green-colored leaves; dark red-colored flower bracts; early flowering habit; excellent post-production longevity; and relatively tolerant to low temperatures.

1 Drawing Sheet

Botanical denomination: *Euphorbia pulcherrima* Willd.
Cultivar designation: 'Stargazer'.

BACKGROUND OF THE INVENTION

The present Invention relates to a new and distinct cultivar of Poinsettia plant, botanically known as *Euphorbia pulcherrima* Willd., and hereinafter referred to by the cultivar name 'Stargazer'.

The new Poinsettia is a product of a planned breeding program conducted by the Inventor in Aalsmeer, The Netherlands. The objective of the breeding program is to create new Poinsettia cultivars with upright and uniform plant habit, attractive flower bract shape and coloration, low temperature tolerance and good postproduction longevity.

The new Poinsettia originated from a cross-pollination made by the Inventor on Jan. 15, 2000 of a proprietary selection of *Euphorbia pulcherrima* Willd. identified as code number 98025, not patented, as the female, or seed, parent, with a proprietary selection of *Euphorbia pulcherrima* Willd. identified as code number 98001, not patented, as the male, or pollen, parent. The cultivar Stargazer was discovered and selected by the Inventor on Nov. 16, 2000 as a flowering plant within the progeny of the stated cross-pollination in a controlled environment in Aalsmeer, The Netherlands.

Asexual reproduction of the new Poinsettia by vegetative terminal cuttings in a controlled environment in Aalsmeer, The Netherlands since July, 2001, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Stargazer'. These characteristics in combination distinguish 'Stargazer' as a new and distinct Poinsettia cultivar:

1. Upright and uniform plant habit.
2. Vigorous growth habit.
3. Dark green-colored leaves.
4. Dark red-colored flower bracts.
5. Early flowering habit; response time, about seven weeks.
6. Excellent post-production longevity.
7. Relatively tolerant to low temperatures.

Plants of the new Poinsettia differ from plants of the female parent selection in the following characteristics:

1. Plants of the new Poinsettia have more intense red-colored flower bracts than plants of the female parent selection.
2. Plants of the new Poinsettia are tolerant to lower temperatures than plants of the female parent selection.

Plants of the new Poinsettia differ from plants of the male parent selection in the following characteristics:

1. Plants of the new Poinsettia have longer postproduction longevity than plants of the male parent selection.
2. Plants of the new Poinsettia are tolerant to lower temperatures than plants of the male parent selection.

Plants of the new Poinsettia can be compared to plants of the cultivar Fiscor, disclosed in U.S. Plant Pat. No. 9,364. In side-by-side comparisons conducted in Aalsmeer, The Netherlands, plants of the new Poinsettia differed from plants of the cultivar Fiscor in the following characteristics:

1. Plants of the new Poinsettia had stronger stems and were sturdier than plants of the cultivar Fiscor.
2. Flower bract color of plants of the new Poinsettia was more intense red than flower bract color of plants of the cultivar Fiscor.
3. Plants of the new Poinsettia had longer postproduction longevity than plants of the cultivar Fiscor.
4. Plants of the new Poinsettia are tolerant to lower temperatures than plants of the cultivar Fiscor.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a single flowering plant of 'Stargazer' grown in a container.

DETAILED BOTANICAL DESCRIPTION

Plants of the new Poinsettia have not been observed under all possible environmental conditions. The phenotype may vary somewhat with variations in environment such as temperature, daylength and light intensity, without, however, any variance in genotype.

The aforementioned photograph, following observations and measurements describe plants grown in De Kwakel, The Netherlands during the fall under commercial practice in a glass-covered greenhouse with day and night temperatures averaging the first ten weeks at 20° C., day and night temperatures averaging the last weeks of production at 17° C.; and light levels of about 200 W/m$^2$. Cuttings were planted into 13-cm containers when rooted and pinched once. Plants were flowered under short day/long night (15 hour nyctoperiods) conditions. Plants were about 17 to 18 weeks from unrooted cuttings when the photograph and the detailed botanical description were taken. In the following description, color references are made to The Royal Horticultural Society Colour Chart, 1995 Edition, except where general terms of ordinary dictionary significance are used.

Botanical classification: *Euphorbia pulcherrima* Willd. cultivar Stargazer.

Parentage:

*Female, or seed, parent.*—Proprietary selection of *Euphorbia pulcherrima* Willd. identified as code number 98025, not patented.

*Male, or pollen, parent.*—Proprietary selection of *Euphorbia pulcherrima* Willd. identified as code number 98001, not patented.

Propagation:

*Type cutting.*—Vegetative terminal cuttings.

*Time to initiate roots.*—Summer: About 10 days at 22° C. Winter: About 14 days at 22° C.

*Time to produce a rooted cutting.*—About four weeks at 22° C.

*Root description.*—Fibrous; freely-branching; white in color.

Plant description:

*Growth habit.*—Upright and uniform plant habit; inverted triangle; top of plant rounded; rapid growth rate and vigorous growth habit.

*Plant height.*—About 25 cm.

*Plant diameter or spread.*—About 30 cm.

*Lateral branch description.*—Quantity per plant: Lateral branches potentially developing at every node after pinching. Length: About 12 to 16 cm. Diameter: About 6 mm. Internode length: About 5 to 15 mm. Texture: Smooth, glabrous. Strength: Very strong; sturdy plants. Color: Close to 144A.

*Foliage description.*—Arrangement: Alternate, single. Quantity of leaves: About eight per lateral branch. Length: About 11 cm. Width: About 8 cm. Shape: Ovate. Apex: Acute. Base: Cuneate to obtuse. Margin: Entire or slightly irregularly lobed. Venation pattern: Pinnate. Texture, upper and lower surfaces: Glabrous, smooth; leathery. Color: Developing foliage, upper surface: Close to 144A. Developing foliage, lower surface: Close to 144B. Fully expanded foliage, upper surface: Close to 147A. Fully expanded foliage, lower surface: Close to 147B. Venation, upper and lower surfaces: Similar to lamina. Petiole: Length: About 6.5 cm. Diameter: About 2 mm. Texture, upper and lower surfaces: Glabrous, smooth. Color, upper and lower surfaces: Close to 183B.

Inflorescence description:

*Inflorescence type and habit.*—Inflorescences are compound corymbs of cyathia with colored flower bracts subtending the cyathia. Inflorescences not persistent.

*Fragrance.*—None detected.

*Natural flowering season.*—Autumn/winter; flower initiation and development is induced under short day/long night conditions.

*Response time.*—Early flowering, about seven weeks.

*Post-production longevity.*—Plants of the new Poinsettia maintain good substance and bract color for about six weeks under interior conditions and about eight weeks under greenhouse conditions.

*Quantity of inflorescences.*—One per lateral branch; typically about five to seven per plant.

*Inflorescence size.*—Diameter: About 21 cm. Height (depth): About 5 cm.

*Flower bracts.*—Quantity of fully developed flower bracts: About twelve per inflorescence. Length: About 10 cm. Width: About 6 cm. Shape: Ovate. Apex: Acuminate. Base: Obtuse. Margin: Mostly entire. Texture, upper and lower surfaces: Glabrous, smooth; leathery. Color: Developing bracts, upper surface: Slightly darker than 53C. Developing bracts, lower surface: 53C. Fully expanded bracts, upper surface: 53B. Fully expanded bracts, lower surface: Lighter than 53B. Venation, upper and lower surfaces: Same as lamina. Bract petiole: Length: About 2 to 3 cm. Diameter: About 2 mm. Texture, upper and lower surfaces: Glabrous, smooth. Color, upper and lower surfaces: Close to 183B.

*Cyathia.*—Quantity of cyathia: About five per corymb. Diameter of cyathia cluster: About 1.5 to 2 cm. Length: About 1 cm. Diameter: About 5 mm. Shape: Oval. Color, immature and mature: Close to 144B.

*Nectaries.*—Quantity of nectaries: One per cyathium. Diameter: About 5 mm. Color: 24B.

*Peduncle.*—Length: About 5 mm. Diameter: About 1 mm. Aspect: Erect. Strength: Strong. Texture: Glabrous, smooth. Color: Close to 144A.

*Reproductive organs.*—Stamens: Quantity of stamens: About eight per cyathium. Anther shape: Rounded. Anther length: About 0.5 mm. Anther color: Close to 183B. Amount of pollen: Moderate. Pollen color: Close to 9A to 12A. Pistils: Quantity of pistils: Three per cyathium. Pistil length: About 5 mm. Style length: About 2 mm. Style color: 45C. Stigma shape: Bi-parted. Stigma color: 45C.

Disease/pest resistance: Resistance to pathogens and pests common to Poinsettias has not been observed on plants grown under commercial conditions.

Temperature tolerance: Plants of the new Poinsettia have been observed to be relatively tolerant to low temperatures and to tolerate temperatures ranging from 17 to 35° C.

It is claimed:

1. A new and distinct cultivar of Poinsettia plant named 'Stargazer', as illustrated and described.

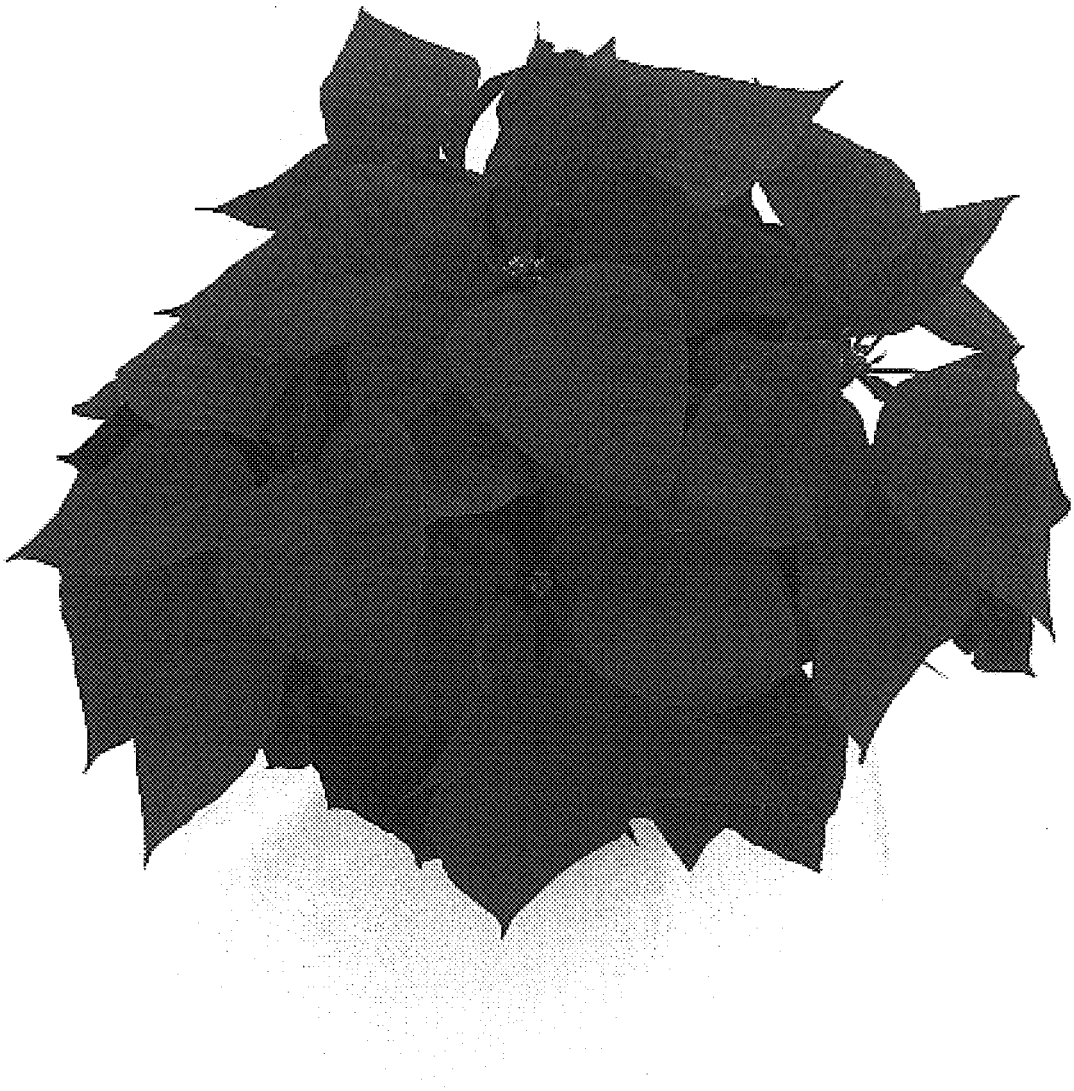

* * * * *